(12) United States Patent
Breemhaar et al.

(10) Patent No.: US 11,512,273 B2
(45) Date of Patent: Nov. 29, 2022

(54) APPARATUS AND PROCESS FOR PRODUCTION OF TISSUE FROM CELLS

(71) Applicant: Mosa Meat B.V., Maastricht (NL)

(72) Inventors: Jonathan Jan Breemhaar, Boskoop (NL); Mark Post, Berg en Terblijt (NL)

(73) Assignee: MOSA MEAT B.V., Maastricht (NL)

( * ) Notice: Subject to any disclaimer, the term of this patent is extended or adjusted under 35 U.S.C. 154(b) by 1205 days.

(21) Appl. No.: 16/007,943

(22) Filed: Jun. 13, 2018

(65) Prior Publication Data
US 2019/0338232 A1 Nov. 7, 2019

(51) Int. Cl.
  *C12M 1/12* (2006.01)
  *C12M 1/00* (2006.01)
  *C12M 1/26* (2006.01)
  *C12N 5/077* (2010.01)

(52) U.S. Cl.
  CPC ............ *C12M 25/10* (2013.01); *C12M 25/14* (2013.01); *C12M 29/00* (2013.01); *C12M 33/00* (2013.01); *C12N 5/0658* (2013.01); *C12N 2506/13* (2013.01); *C12N 2506/1392* (2013.01)

(58) Field of Classification Search
  CPC ...... C12M 25/10; C12M 25/14; C12M 29/00; C12M 33/00; C12M 23/24; C12M 23/08; C12M 23/34; C12M 25/06; C12N 5/0658; C12N 2506/13; C12N 2506/1392
  See application file for complete search history.

(56) References Cited

U.S. PATENT DOCUMENTS

| 9,249,383 | B2* | 2/2016 | Yu ........................... C12M 23/46 |
| 2008/0044900 | A1* | 2/2008 | Mooney ......... A61K 39/001182 435/402 |
| 2009/0298163 | A1 | 12/2009 | Bennett et al. |
| 2011/0263021 | A1* | 10/2011 | Stobbe ................ F04B 43/0736 435/243 |
| 2013/0029008 | A1 | 1/2013 | Forgacs et al. |
| 2014/0199679 | A1* | 7/2014 | Panoskaltsis ........ C12N 5/0641 435/297.1 |
| 2016/0227830 | A1* | 8/2016 | Genovese ............ C12N 5/0658 |
| 2016/0227831 | A1* | 8/2016 | Marga ..................... A23L 13/00 |

FOREIGN PATENT DOCUMENTS

| KR | 101378014 B1 | 3/2014 |
| WO | 2011161086 A2 | 12/2011 |

OTHER PUBLICATIONS

Reis Passinhas, Dora; Written Opinion for International Patent Application No. PCT/EP2019/060744, dated Jun. 28, 201, 9 pages.
Dixon, Laura; Combined Search and Examination Report for United Kingdom Patent Application No. GB1807326.2, dated Jul. 25, 2018, 6 pages.

* cited by examiner

*Primary Examiner* — Titilayo Moloye
*Assistant Examiner* — Suzanne E Ziska

(57) ABSTRACT

Disclosed is an apparatus for the production of tissue from cells. The apparatus comprises an elongate body having at least one circumferential groove and being operable to extend, by close-fitting relationship, centrally through at least one trough. The troughs are extending in a closed path, such that the at least one of the circumferential grooves open into an inner edge of a trough.

Also disclosed is a process for production of tissue from cells, via a transitioning intermediate which transitions from the cells into the tissue.

20 Claims, 10 Drawing Sheets

APPARATUS AND PROCESS FOR PRODUCTION OF TISSUE FROM CELLS

TECHNICAL FIELD

The present disclosure relates generally to muscle production; and more specifically, to an apparatus for production of tissue from cells and a process for production of tissue from cells using the aforementioned apparatus.

BACKGROUND

Since ancient times, meat has been a major source of high-quality protein in the human diet, and to this day it continues to provide nutrition to the exponentially growing population of the world. However, meat is a very inefficient source of food and its production has increased so much that it is now one of the largest contributors to a number of serious problems. First of all, meat production is one of the largest contributors to human-induced climate changes. The main reason for this are methane emissions from ruminants and nitrous gasses that are released from fertilizer/manure and from soil after deforestation. In addition to that, meat production is also associated with animal welfare, pollution and food safety issues. It is expected that by 2050 the demand for meat will have increased by 70%. Therefore, there is a need for a more sustainable alternative to meat.

However, more than 90% of the global population is so meat-dependent that we find it extremely hard to remove it from our diet. Meat substitutes from plants and other sustainable protein sources have been around for decades, and are improving through advancing technology, but are still not accepted as meat replacement by the majority of the society.

The ideal replacement for animal meat would be meat produced through tissue engineering. Virtually all aforementioned downsides of meat production would be eradicated but the consumers could still enjoy the meat.

Growing muscle tissue has been subject to research & development for a long time in the medical and research field, and conducted by artificially proliferating two-dimensional (2D) muscle cells into three-dimensional (3D) tissue-specific progenitors in the presence of growth and differentiation media.

However, even current tissue engineering fails as a technology to potentially produce meat for several reasons:

Firstly, the cells that are needed to grow muscles are still grown with the use of foetal calf serum (FCS), an extremely animal unfriendly and also relatively scarce substance; also, tissue formation typically makes use of gels that facilitate tissue formation, commonly collagen, which is animal derived. The process needs to be made animal-free (except the initial cell sample).

Also, the tissue formation process as it is currently done in the medical or research field is typically very labour intensive and therefore economically not viable for mass production.

In the search for a tasty, cruelty-free and nutritious meat product, produced in an efficient manner, there is a strong need to develop an automated and scalable bio artificial muscle production process.

SUMMARY

The present disclosure seeks to provide an apparatus for production of tissue from cells. The present disclosure also seeks to provide a process for production of tissue from cells via the aforementioned apparatus. The present disclosure seeks to provide a solution to the existing problems such as difficulty in scalability of bio artificial muscle production from cultured cells. An aim of the present disclosure is to provide a solution that overcomes at least partially the problems encountered in prior art and provides an effective and much more sustainable alternative for traditional meat.

In one aspect, an embodiment of the present disclosure provides an apparatus for the production of tissue from cells. The apparatus comprises an elongate body having at least one circumferential groove and being operable to extend, by close-fitting relationship, centrally through at least one trough, at least one trough extending in a closed path, at least one of the circumferential grooves opening into an inner edge of a trough.

In another aspect, an embodiment of the present disclosure provides a process for the production of tissue from cells, via a transitioning intermediate which transitions from the cells into the tissue, the process comprising:
 a. providing an apparatus according to any one of the preceding claims;
 b. adding the cells and a liquid hydrogel, comprising a scaffolding biomaterial, into at least one trough of the apparatus;
 c. cross-linking the scaffolding biomaterial;
 d. applying a differentiation medium to the transitioning intermediate; and
 e. incubating the transitioning intermediate in the differentiation medium to form tissue comprised in a ring in the at least one circumferential groove.

Embodiments of the present disclosure substantially eliminate or at least partially address the aforementioned problems in the prior art, and enables efficient production of bio artificial muscle, while being substantially less labour-intensive. Moreover, the present disclosure enables a larger scale of production of tissue than offered by the prior art.

Additional aspects, advantages, features and objects of the present disclosure would be made apparent from the drawings and the detailed description of the illustrative embodiments construed in conjunction with the appended claims that follow.

It will be appreciated that features of the present disclosure are susceptible to being combined in various combinations without departing from the scope of the present disclosure as defined by the appended claims.

BRIEF DESCRIPTION OF THE DRAWINGS

The summary above, as well as the following detailed description of illustrative embodiments, is better understood when read in conjunction with the appended drawings. For the purpose of illustrating the present disclosure, exemplary constructions of the disclosure are shown in the drawings. However, the present disclosure is not limited to specific methods and instrumentalities disclosed herein. Moreover, those skilled in the art will understand that the drawings are not to scale. Wherever possible, like elements have been indicated by identical numbers.

Embodiments of the present disclosure will now be described, by way of example only, with reference to the following diagrams wherein.

Figure 1:
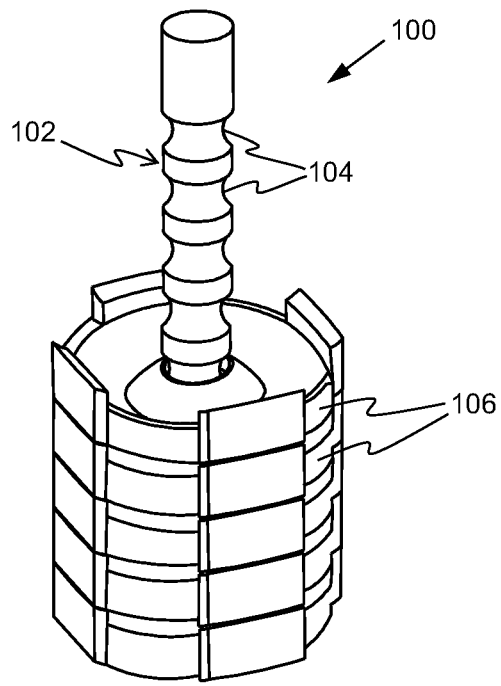
FIG. 1 is a perspective view of an apparatus for the production of tissue from cells, in accordance with an embodiment of the present disclosure.

In the accompanying drawings, an underlined number is employed to represent an item over which the underlined number is positioned or an item to which the underlined number is adjacent. A non-underlined number relates to an item identified by a line linking the non-underlined number to the item. When a number is non-underlined and accompanied by an associated arrow, the non-underlined number is used to identify a general item at which the arrow is pointing.

DETAILED DESCRIPTION OF EMBODIMENTS

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The present disclosure provides an apparatus for the production of tissue from cells. Beneficially, the apparatus is efficient and less labour-intensive. Furthermore, the apparatus enables in production of a more sustainable alternative for standard meat. In other words, the bio artificial muscle produced using the apparatus ensures improved quality, i.e. required uniformity for the produced bio artificial meat. The uniformity of the bio artificial muscle simulates the standard meat in terms of its appearance, texture and flavour. Further, the bio artificial muscle delivers the same consumer experience at a competitive price.

The present disclosure provides a process for the production of tissue from cells, using the aforementioned apparatus. Beneficially, the apparatus is efficient and less labour-intensive. Furthermore, the apparatus provides a more sustainable alternative to the standard meat. In other words, the bio artificial muscle produced using the apparatus ensures uniformity throughout the product. The uniformity in the product simulates the standard meat in terms of its appearance, texture and flavour, while delivering the same consumer experience at a competitive price.

The present disclosure provides an apparatus for the production of tissue from cells, the apparatus comprising an elongate body having at least one circumferential groove and being operable to extend, by close-fitting relationship, centrally through at least one trough, the at least one trough extending in a closed path, at least one of the circumferential grooves opening into an inner edge of a trough.

Throughout the present disclosure, the term "elongate body" used herein relates to a three-dimensional (3D) support structure composed of natural or synthetic material. The elongate body may be composed of, but not limited to, stainless steel, or a plastics material such as acetal, nylon, polybutylene terephthalate or polylactic acid, preferably each material is provided as a medical grade material. The elongate body is designed to act as an anchor for the bio artificial muscle tissue produced from muscle cells. Optionally, the elongate body may contain a number of variable shapes and dimensions. The variable shapes and dimensions may be optimized to assure an ideal structure for the proliferation of the cells and preventing breakage of the cross-linking cells.

It may be noted that length of the elongate body may be optimized to determine the productivity of the apparatus and process. It is evident that longer elongated body hold a higher amount of bio artificial product. However, to avoid limitations that may occur by material deformation or increased obstruction while moving in or out (placing or retracting) the elongate body, an approximately 20 millimetres to 1000 millimetre long elongate body may be used. Optionally, apart from the length of the elongate body, diameter of the elongate body may also be required to be optimized. It will be appreciated that a larger diameter may induce more tensile stress in the final tissue, the tensile stress being important in the differentiation process. Therefore, a typical diameter of the elongate body may be optimized as 2 millimetres to 10 millimetres.

More optionally, the elongate body may be in the form of a pillar. In an example, the elongate body may be a cylindrical-shaped pillar, an oval-shaped or an elliptical-shaped pillar. Specifically, pillars enable the bio artificial muscle to form encircling and not adhering to the pillars. This ensures maintenance of the structure and less wastage of the bio artificial muscle. However, the elongate body with the desired product formed therearound, may experience hindrance at the stage of retraction. Such hindrance may result in an accidental breakage of the desired product, so the elongate body may be designed to prevent accidental breakage by providing at least one circumferential groove in the elongate body or optimization of the shape of the elongate body. In this regard, the elongate body may be made of a flexible material. In an embodiment, the elongate body may have a flexible surface layer. Beneficially, the elongate body made of flexible material or may have a flexible surface layer to support the structure of the desired product. Optionally, the elongate body may be edible, or at least the surface layer may be made of an edible material.

The elongate body comprises an at least one circumferential groove and is operable to extend, by close fitting relationship, centrally through at least one trough, the at least one trough extending in a closed path, at least one of the circumferential grooves opening into an inner edge of a trough. The elongate body is optimized for an appropriate size and shape, comprising at least one circumferential groove, to extend centrally through the at least one trough and fit into the defined place. Optionally, each circumferential groove may be optimized to an indent depth (or thickness) of 800 microns. It is preferred that the depth of the indent of the circumferential groove is sufficient to accommodate the thickness of the bio artificial muscle produced. Additionally, the vertically-adjacent circumferential grooves, along the length of the elongate body, may be separated by a distance comparable to the vertical spacing between the vertically-adjacent troughs of the apparatus. Furthermore, less spacing between the circumferential grooves results in larger amounts of bio artificial muscle production per length of pillar.

Optionally, each of the circumferential grooves opens into the inner edge of a trough. Throughout the present disclosure, the term "trough" used herein relates to a well for holding the starting biomaterial for the production of tissue. It may be noted that each of the at least one trough is designed to have a central hole. Optionally, the central hole in each of the at least one trough may be circular-shaped, cylindrical-shaped, an oval-shaped or an elliptical-shaped. Further, the elongate body having at least one circumferential groove is operable to extend, by close-fitting relationship, through the central hole of the at least one trough.

The at least one trough is designed to extend in a closed path. The closed path can be of any shape to match the cross-sectional shape of the elongate body or pillar. In an embodiment, the closed path is elliptical.

In another embodiment, the closed path is a circle. The at least one trough may be a circular well designed to hold starting biomaterial or the initial cells, derived from a selected donor organism for the production of tissue. Therefore, when the troughs extend in a closed path that is a circle, the aforementioned apparatus provides an at least one circular trough surrounding the elongate body.

In an embodiment, the closed path may be stadium-shaped. The stadium-shaped closed path may be designed to provide a trough constructed of a rectangle with semi-circles at a pair of opposite sides of the rectangle. Furthermore, the stadium-shaped trough resembles a capsule. Thus, when the troughs extend in a closed path that is stadium-shaped, the aforementioned apparatus provides an at least one trough shaped like a track of a stadium surrounding the elongate body.

Optionally, the at least one trough has an outer wall, an outer edge, an inner edge, and a sloping wall. More optionally, the at least one trough has a sloping wall extending from a low region of the trough to the inner edge, and an outer wall extending from the low region to an outer edge of the trough. Further, more optionally, the outer wall may be vertical with an outwards bending slope, while the sloping wall extending to the inner edge may be curved and inclined at an angle, preferably inclined at an angle of 45 degrees (or 45°). Such sloping assists migration of a ring of biomaterial out of the trough during processes of the disclosure. Beneficially, the closed path of the trough, and optimized heights (namely, depths) of the walls, ensures that the starting biomaterial or the initial cells, derived from a selected donor organism, for the production of tissue are not leaked from the trough. Optionally, the depth of each of the troughs may be range from 40 microliters to 1000 microliter. The troughs may be made of any suitable material, such as stainless steel or plastics such as acetal, nylon, polystyrene, polybutylene terephthalate or polylactic acid. They may be formed by stamping, injection moulding, vacuum forming or CNC milling.

In other words, when the elongate body extends centrally through the at least one trough and fits into the defined place, wherein the at least one of the circumferential grooves opens into an inner edge of a trough. Such a configuration of the circumferential groove in relation to the inner edge of the corresponding trough enables a ring of biomaterial migrating from the trough to be guided by its own developing tension into the circumferential groove.

Optionally, the elongate body extends, by close-fitting relationship, centrally through at least one trough, at least one of the circumferential grooves opening into an inner edge of a trough. The elongate body extends in its defined position centrally through the at least one trough, so that at least one of the circumferential grooves of the elongate body aligns with the inner edge of the at least one troughs. Each circumferential groove of the elongate body may be aligned in a corresponding defined position relative to an adjacent trough. In an example, a first circumferential groove is aligned with a first trough, wherein the first circumferential groove is placed at lower end of the elongate body and the first trough is located at the bottom of the aforementioned apparatus. Similarly, a second circumferential groove is aligned with a second trough, wherein the first circumferential groove is located above the first circumferential groove separated by a portion of the elongate body (not the circumferential groove), and the second trough is located above the first trough separated by a predefined vertical spacing between the first and the second troughs.

Optionally, at least one elongate body, with separate elongate bodies extends respectively through separate of the at least one trough. As mentioned previously, the elongate body extends centrally through the at least one trough. However, separate elongate bodies may also be extended respectively through separate of the at least one trough. The separate elongate bodies may include, but not limited to, a pipe for filling (and/or re-filling) the starting biomaterial for the production of tissue therefrom, a medium (such as a growth and/or a differentiation medium), additional growth factors, and so forth. The separate elongate bodies may be extended through separate passages (or central holes) of the at least one trough. Optionally, the elongate bodies may have side ports at predefined distance that enables it to pour its contents in the adjacent troughs.

Optionally, the elongate bodies, such as a pipe, may have a closed end and side ports near the closed end, the pipe operable to extend through the at least one through-hole in the at least one or more troughs of the apparatus. More optionally, the pipe may be moved through the at least one through-hole to align the side port with the at least one trough for performing the desired function of transferring the starting biomaterial for the production of tissue therefrom, a medium (such as a growth and/or a differentiation medium), additional growth factors, and so forth.

In an embodiment, the one or more separate elongate bodies may be placed inside an elongate body in a concentric arrangement, wherein the elongate body houses a pipe. Optionally, the elongate bodies, such as a pipe, may have a longitudinal internal channel and side holes positioned to open from the internal channel into circumferential grooves of the elongate body. Subsequently, such concentric arrangement may be moved through the central hole and aligned with the at least one trough for performing the desired function.

Optionally, the close-fitting relationship between the elongate body and the at least one trough comprises a sliding engagement. The elongate body is extended through the at least one trough by sliding the former in the latter. In other words, the close-fitting relationship, that governs the extending of the elongate body ensures defined positioning of the elongate body centrally though the at least one trough. Specifically, the at least one of the circumferential grooves of the elongate body is aligned in a manner that it opens into the inner edge of an adjacent at least one trough. More specifically, such alignment is achieved by sliding the elongate body centrally though the at least one troughs.

Optionally, the troughs are joined edgewise outside their outer walls to laterally-adjacent troughs whereby separate elongate bodies extend through the trough and the laterally-adjacent trough. The at least one troughs are joined to their laterally-adjacent troughs by their outer walls. The separate elongate bodies may extend through the trough and the void formed by the placement of four horizontally-placed toughs. For example, a first trough is joined edgewise to a second trough through their outer walls, wherein the second trough is placed laterally-adjacent to the first trough. Similarly, a third trough is joined edgewise with the second trough through their outer walls. Further, a fourth trough is joined edgewise with the first trough and the third trough through their respective outer walls.

Optionally, the troughs joined edgewise are formed as a unitary component, the unitary component having a top surface and a bottom surface. In the above example, it may be noted that the four laterally-adjacent troughs, joined edgewise outside their outer walls, form a plate-like arrangement, referred to as a unitary component of troughs, comprising a single common top surface and a single common bottom surface. Furthermore, the unitary component has at least one through-hole communicating between the top surface and the bottom surface, the through-hole located outside the outer walls of the troughs. In the above example, it may be noted that the unitary component comprising the first trough, the second trough, the third trough and the fourth trough, created a through-hole between the laterally-adjacent four troughs. The through-hole connects the single common top surface and the single common bottom surface of the unitary component of troughs. It is evident that the through-hole is located outside the outer walls of the laterally-adjacent troughs.

Optionally, at least one trough is stacked. The plurality of troughs may be arranged vertically in a stack. More optionally, the at least one trough is provided with vertically extending spacers to provide distance between adjacently stacked troughs. As mentioned previously, the vertically stacked plurality of troughs may be separated by vertically extending spacers to provide distance between adjacently stacked troughs. Optionally, such vertically extending spacers may be used to create a distance of 1 millimetre to 5 millimetres between the vertically-adjacent troughs.

Optionally, the at least one unitary component of troughs joined edgeways, said unitary components being joined vertically to provide a grand unitary component, by joining the respective top surfaces of troughs of a unitary component with corresponding bottom surfaces of troughs of an above-adjacent unitary component. Multiple unitary components of troughs joined vertically in a stack form the grand unitary component of troughs. Such vertical stacking of multiple unitary components of troughs is achieved by joining the respective top surfaces of troughs of one unitary component with the corresponding bottom surfaces of troughs of another above-adjacent unitary component. For example, the steps of a ladder are joined together to provide a unitary ladder, wherein, the steps are reflective of the vertically stacked troughs and the ladder is reflective of the grand unitary component. Optionally, the grand unitary component may be manufactured by 3D printing or by welding together unitary components in a stack.

Optionally, the elongate body has a longitudinal groove of at least the depth of the at least one circumferential groove. It will be appreciated that a long elongate body allows for formation of multiple bio artificial muscles (BAMs) around it, and thereby simplifying the harvesting and cutting of the bio artificial muscles (BAMs) from the elongate body. Beneficially, a large number of bio artificial muscles (BAMs) may be harvested by a single movement of a cutter along the longitudinal groove of the elongate body. Additionally, employing long elongate body eliminates the need for a multiple precise and excessive cutting movements while still reaping the benefits.

Optionally, the elongate body and the troughs of the apparatus may be placed in a container for the production of tissue from the cells. More optionally, at least one or more containers may be provided, specifically for different phases of the said production. Specifically, the elongate body may be removed from the said container and placed in another container for different periods of incubation. The at least one container may contain a growth medium and/or a differentiation medium. Further, the container may be designed for receiving and draining the growth medium and/or a differentiation medium to assist in the production of tissue from cells.

The present disclosure also relates to a process for the production of tissue from cells, via a transitioning intermediate which transitions from the cells into the tissue.

The aforementioned process contributes to ensuring a quality product with appropriate thickness for combating the issues related to a necrotic core in the inner cells of the muscle and reduces environmental impacts and cruelty towards animals relative to the conventional methods. Additionally, the present disclosure aims towards reducing the number of steps and parts of the apparatus necessary for the mass production of tissue from cells. Furthermore, the process may be easily up-scaled and operated through automation with minimum error. Furthermore, the process also aims towards decreasing the total volume of the differentiation medium necessary for submerging the elongate body having rings of biomaterial in the multiple circumferential grooves therein.

The process for the production of tissue from cells, via a transitioning intermediate which transitions from the cells into the tissue, comprises providing the aforementioned apparatus for the production of tissue from cells.

Throughout the present disclosure, the term "cell" as used herein, refers to a starting material received from a donor organism. The cell comprises a cell membrane, at least one chromosome, composed of genetic material, and a cytoplasm. Furthermore, the cell comprises various organelles which are adapted or specialized to perform one or more vital functions, such as energy and proteins synthesis, respiration, digestion, storage and transportation of nutrients, locomotion, cell division, and so forth. Optionally, the cells may be selected from at least one of the group consisting of mesenchymal cells, myoblasts and myocytes. More optionally the cells may include, but not limited to, mesenchymal cells, muscle cells (myoblasts and myocytes), fat cells, somite cells, cartilage cells, blood cells, or stem cells. The cell divides by way of mitosis or meiosis yielding 2 or 4 daughter cells containing segregated genetic material, respectively.

A small number of initial cells (or starting biomaterial), derived from a selected donor organism (namely, an animal), may be used to initiate cell division. Optionally, the production of edible animal tissue, where the animal is selected from cattle, pig, sheep, poultry, duck, deer, rabbit, fish or other seafood. More optionally, the donor organism may be selected from a livestock species (such as cow, buffalo, sheep, goat, pig, camel, rabbit, deer, and the like), poultry species (such as chicken, goose, turkey, pheasant, duck, ostrich, and the like), and/or aquatic or semi-aquatic species (such as fish, molluscs (namely, abalone, clam, conch, mussel, oyster, scallop, and snail), cephalopods (namely, cuttlefish, octopus, and squid), crustaceans (namely, crab, crayfish, lobster, prawn, and shrimp), cetaceans, frog, turtles, crocodiles, and the like. It will be appreciated that the donor animals are kept under strictly hygienic conditions in order to receive a good quality of initial cells. Furthermore, the cell division is followed by cell growth and differentiation into various functional components, namely, tissues, for carrying out different activities.

Optionally, the said process may be used for the production of human or animal tissue. The tissue so produced by such process via the said apparatus may be used for various purposes, such as in medicine, surgery, food industry, leather industry, and so forth.

Throughout the present disclosure, the term "tissue" used herein refers to an ensemble of similar cells together with their extracellular matrix. The tissue is an intermediate between a cell and an organ of an organism, adapted to perform specific function. The tissues may be classified into four categories: connective, muscle, nervous and epithelial. In an example, multiple tissues may be functionally grouped to produce an organ.

Optionally, the cells are myoblasts, and the process further comprises proliferation of the myoblasts, by providing a surface to anchor the myoblasts and incubating them in a growth medium, prior to adding the myoblasts in a mixture with a liquid hydrogel comprising a scaffolding biomaterial into the at least one trough of the apparatus. The production of tissue from the cells occurs in a right environment, such as an optimum temperature, access to nutrition and an attachment surface for the cells to relay information about the spatial position of the cell. Such attachment surface may be the extracellular matrix (ECM) of the cells in-vivo. The extracellular matrix (ECM) in the present disclosure is composed of a hydrogel comprising a scaffolding biomaterial that has been crosslinked. Examples of suitable scaffolding biomaterials are proteins and polysaccharides produced by the various organelles of the nearby cells. Other examples are described later, and some do not need to be harvested from animal tissue. When the extracellular matrix (ECM) is arranged at an appropriate side of the cells, such as basal or apical, it provides an attachment surface to the cells, thereby supporting tissue culture and structure. The cells are enabled to develop and change their morphology, for example becoming myofibers. Such process is referred to as differentiation process, where the cells grow and differentiate into specialized tissues.

For example, muscle cells (namely, myocytes) grow and differentiate into muscle tissue. Muscle cells are multinucleate, long and slender and resemble fibres, and often called muscle fibres or myocytes. The muscle cells (or muscle fibres or myocytes) develop from the fusion of myoblasts into myotubes, multinucleated fibres. The myoblasts are a type of embryonic progenitor cells that capable of differentiating into muscle cells in the presence of fibroblast growth factor (FGF), while the myotubes form the basis of muscle tissue. The muscle tissue may be classified as skeletal muscle tissue (multinucleate), smooth muscle tissue (mono-nucleate) and cardiac muscle tissue (mono-nucleate).

The process further comprises adding the cells and a liquid hydrogel, comprising a scaffolding biomaterial, into at least one trough of the apparatus. The muscle cells (myoblasts and myocytes) are added to a liquid hydrogel. The term "hydrogel" used herein refers to hydrophilic, natural or synthetic polymeric networks extensively dispersed in water, but rendered insoluble due to different types of crosslinking mechanism therein. The hydrogels are highly reflective of the natural tissues due to their ability to absorb and retain water. The hydrogel may be synthesized from natural or synthetic components, and thereby accordingly depict different levels of functionality and degradability. The hydrogel comprises a three-dimensional network of polymer components and water filling space between the polymeric macromolecules. The hydrogels may be homopolymeric, copolymeric or multipolymer interpenetrating polymeric hydrogels (IPN) depending on the type of polymeric network derived from a single species of monomer, two or more different monomer species, or two independent cross-linked synthetic and/or natural polymer component respectively. The hydrogel may be, but not limited to, collagen, elastin-like polypeptides, tropoelastin, hyaluronic acid, alginate, polyvinyl alcohol (PVA), polycaprolactone (PCL), synthetic DNA hydrogel, and so forth.

Furthermore, the hydrogel may comprise a scaffolding biomaterial that are highly reflective of the extracellular matrix (ECM) and aids in cell attachment and proliferation.

The cells may conveniently be added to the liquid hydrogel before adding into the at least one trough. Specifically, proper mixing the cell and the liquid hydrogel ensures cells to attach to the scaffolding biomaterial within the hydrogel. The term "scaffolding biomaterial" used herein refers to an array of natural or synthetic matrix molecules to which cells can attach. The natural scaffolding biomaterial may be a plant-based material or an animal-based two-dimensional (2D) or three-dimensional (3D) structure. The scaffolding biomaterial may be composed of a highly porous material that provides maximal surface area for cell attachment and growth. Optionally, the scaffolding biomaterial may be collagen type I, elastin, fibrin, proteoglycans, polyurethane, polylactic acid, pectin, chitin, hyaluronan and oligomers thereof, microparticles, liposomes, Matrigel™, and so forth.

Optionally, the at least one trough is filled with the mixture to a depth level with the inner edge of the at least one trough when adding cells and the hydrogel therein. It will be appreciated that the height of the inner edge is optimized to the height of the starting biomaterial or the initial cells, derived from a selected donor organism, for the production of tissue. The depth level corresponding with the inner edge of the at least one trough ensures that the mixture is not leaked out from the well.

Optionally, mixture of the cells and the liquid hydrogel, comprising a scaffolding biomaterial, may be added to the at least one troughs by providing an elongate body having a longitudinal internal channel and side holes positioned to open from the internal channel into circumferential grooves of the elongate body. Such longitudinal internal channel and side holes positioned to open from the internal channel into the circumferential grooves of the elongate body may be used for transferring the cells in a mixture with a liquid hydrogel comprising a scaffolding biomaterial through the longitudinal channel and side holes into the at least one trough of the apparatus.

In an embodiment, the process comprises adding the cells and a liquid hydrogel comprising scaffolding biomaterial into the at least one trough of the apparatus via the pipe and the side port. Subsequently, the pipe may be moved through the at least one through-hole to align the side port with the at least one trough for adding the cells and a liquid hydrogel comprising scaffolding biomaterial into the at least one trough.

In yet another embodiment, the mixture of the cells and the liquid hydrogel may be added by the pipe that may extend centrally through the at least one trough for filling the mixture of the cells and the liquid hydrogel. Subsequently, the pipe is withdrawn and the elongate body is positioned in the container by extending centrally through the at least one trough.

In yet another embodiment, the apparatus may comprise a pipe and an elongate body, with concentric arrangement and concentric side ports, the concentric arrangement operable to extend centrally through the at least one trough for filling the cells and a liquid hydrogel comprising scaffolding biomaterial into the at least one trough of the apparatus via the pipe and the side port. Subsequently, the pipe and the elongate body may be moved through the central hole and align the side port with the at least one trough for adding the cells and a liquid hydrogel comprising scaffolding biomaterial into the at least one trough. Furthermore, such concentric arrangement of the pipe and the elongate body may be used for both filling and re-filling the at least one troughs with the mixture of cells and the liquid hydrogel comprising a scaffolding biomaterial.

In yet another embodiment, the mixture of the cells and the liquid hydrogel may be added to the at least one troughs by transferring the cells in a mixture with a liquid hydrogel comprising a scaffolding biomaterial into the at least one trough of the apparatus by pipetting. Furthermore, transferring the mixture of the cell and the liquid hydrogel into a trough is carried out followed by stacking an above adjacent trough, sequentially for troughs of the at least one trough. Furthermore, such transferring of mixture of cells and the liquid hydrogel comprising a scaffolding biomaterial may be achieved by pipetting the mixture of the cells and the liquid hydrogel comprising a scaffolding biomaterial for both filling and re-filling the at least one troughs with the mixture of the cells and the liquid hydrogel comprising a scaffolding biomaterial.

In yet another embodiment, the mixture of the cells and the liquid hydrogel may be added by submerging the troughs in a container filled with the mixture of the cells and the liquid hydrogel.

In an embodiment, the pipe may be operable to extend from above and centrally through the at least one trough. In another embodiment, the pipe may be operable to extend from below and centrally through the at least one trough. Optionally, the troughs for filling are filled sequentially from the bottom to the top. Alternatively, or additionally, optionally, the troughs for filling are filled sequentially from the top to the bottom.

Optionally, incubating is carried out at a cell-specific optimal temperature. More optionally, the incubation may be achieved under optimal culture conditions, such as an optimum temperature, for a predefined period of time, and under predefined regulatory conditions. Optionally, the cell-specific optimal temperature is of about 37° C. However, the normal blood temperature of the animal from which original cells were sourced provides a guide to the optimal temperature, such normal blood temperatures being well-known. Furthermore, the incubation is allowed to progress for a couple of days (such as 1 or 2 days), which is suitable for enabling the cells to attach to the scaffolding biomaterial and grow. Optionally, growth medium may be added to the at least one trough. Optionally, the medium enters each trough while slowly rising through the perimeter of the outer edge before flooding the troughs. Such addition of medium ensures that the mixture of the cells and the liquid hydrogel comprising the scaffolding material is not damaged by flooding from a single side.

It will be appreciated that the cells proliferate in a unidirectional manner by subsequent attachment to the matrix of scaffolding biomaterials.

In an embodiment, the mixture comprising cell and the liquid hydrogel, comprising the scaffolding biomaterial, in the container may be fumigated with gas (such as $CO_2$), adjusted to a suitable pH and eventually sealed. Furthermore, addition of amino acid, vitamins, glucose and other growth supplements and medium refreshments (often, batch-wise, usually twice a week, or continuously) as required may be performed once the cells have settled on the scaffolding biomaterials present in the hydrogel.

Furthermore, the growth media and growth conditions may be optimized in a manner known to a person skilled in the art to facilitate the process for production of tissue from cells.

As mentioned previously, the inner edge of the at least one troughs leads to each of the circumferential groove of the elongate body. Therefore, the proliferating cells may grow on, above or within the circumferential groove of the elongate body. Notably, the transitioning intermediate migrates from the at least one trough to the at least one circumferential groove after the scaffolding biomaterial has been cross-linked.

In an example, the scaffolding material provides the early attachment sites for the muscle cells to grow and differentiate into a transitioning intermediate, the myofibers, in the presence of a differentiation medium. The myofibers, further, differentiate into muscle tissue. In the process, the myofibers migrate from the at least one trough to the corresponding circumferential groove of the elongate body.

The process further comprises cross-linking the scaffolding biomaterial. Different types of cross-linking mechanism have been referred to earlier depending on the choice of material in the hydrogel, and these may be promoted, for example, by exposure to heat or ultraviolet radiation. The scaffolding biomaterial, with cells attached thereto, cross-link with each other to assist in the cell growth and proliferation. Furthermore, the cross-linking of scaffolding material may occur in the presence of differentiation medium. It may be noted that the cells entrapped in the above-mentioned bioactive hydrogel proliferate and make a transition of medium. Specifically, the transition of medium refers to the change of medium from the hydrogel (rich in collagen and such likes) to the differentiation medium filled in the container containing the troughs. Consequently, in the presence of the differentiation medium, the reproducible cells differentiate to produce fused myotubes, which further contract (or compact) continuously for 10-12 days to yield the desired bio artificial muscles (BAMs) tissue. It will be appreciated that the compacting cells maintain the adequate cell density and unidirectional cell alignment throughout the tissue depth.

The cells proliferate and differentiate to yield specialized tissues. However, the production of tissue from cells is achieved via a transitioning intermediate which transitions from the cells into the tissue. The term "transitioning intermediate" relates to an intermediate between cells and a corresponding tissue thereof. For example, the process for production of muscle tissue from muscle cells ensures differentiation of mononucleate (single nucleus) muscle cells into multi-nucleate (multiple nucleus) myotubes via a transitioning intermediate.

The process further comprises applying a differentiation medium to the transitioning intermediate. The transitioning intermediate differentiates to yield myotubes that form the basis of muscle tissue. The transitioning intermediate utilizes the nutrients and oxygen from the differentiation medium to proliferate and differentiate into the muscle tissue, while release particulate matter in the process of differentiation. Optionally, the differentiation medium is applied to the mixture in the at least one trough of the apparatus. Optionally, the differentiation medium is rejuvenated after at least one part of the period of incubation, wherein the rejuvenation comprises at least one of i) oxygenation, ii) addition of nutrient, iii) removal of particulate matter, and iv) exchange of the differentiation medium with fresh differentiation medium. Subsequent to the growth of cells into transitioning intermediate, the differentiation medium in the apparatus is required to be replenished for supplying fresh oxygen, nutrients and removal of dead cell debris and other particulate matter. It may be noted that the mixture may be incubated in more than one part of the period of incubation.

Incubation of transitioning intermediate in differentiation medium may be carried out in stages. For example, part of the incubation may be carried out while the transitioning intermediate is in a trough. Furthermore, part of the incubation process may be carried out while the transitioning intermediate is in a circumferential groove before removal of the elongate body from the trough. Part of the incubation process is advantageously carried out while the transitioning intermediate is in a circumferential groove of an elongate body after removal of the elongate body from the trough.

Optionally, the relatively large and thick bio artificial muscles (BAMs) tissue produced at the circumferential groove of the elongate body comprises densely-packed, uniformly-aligned, and highly differentiated myofibres. Such shape and architecture of the bio artificial muscles (BAMs) may be achieved by controlling the spatial distribution of reproducible cells in three-dimensional configuration. The spatial distribution of the proliferating cells is fabricated by the application of specific geometrical constraints. Such guided spatial distribution ensures adequate tissue porosity, size, and thickness of the fabricated bio artificial muscles (BAMs) around the predefined sections of the elongate body. In other words, the ability of the muscle cells to exhibit development of stress fibres and unidirectional cell alignment due to immobilization at one or more surfaces or points of the elongate body results in the fabrication of bio artificial muscles (BAMs) therearound. Optionally, the tissue formed after incubating is in the form of myofibers. The myofiber is a multinucleated single muscle cell that is capable of contracting. The contraction in myofiber is attributed to a network of myofibrils that is composed of actin and myosin myofilaments. The actin and myosin myofilaments slide past each other to produce tension in the muscle cell, thereby producing movement of the body parts. In other words, the cross-linking of the scaffolding material yields the tissue, or in the present case, the myofibers.

Optionally, the specific geometrical constraints as applied from the outer boundary of the bio artificial muscles (BAMs) results in generation of thin muscle bundles or rings comprising of highly aligned cells throughout the entire tissue area.

In an embodiment, differentiation of cells may be sped up by subjecting the ring of biomaterial to electrical pulse stimulation during incubation. Electrical stimulation of the differentiation process speeds up the production of transitioning intermediate.

Optionally, adequate tissue porosity facilitates nutrient and oxygen transport within the relatively thick muscle bio artificial muscles (BAMs) tissue. A continuous nutrient and oxygen supply avoids development of necrotic core of the inner cells of the tissue. In such scenario, the bio artificial muscles (BAMs) mimic the uniformly-aligned architecture of the standard meat in order to produce the same appearance, toughness and taste of the standard meat.

Optionally, the process comprises providing a container for at least a portion of the elongate body, adding differentiation medium into the container, submerging the ring of biomaterial on the elongate body in the differentiation medium in the container, whereby the ring of biomaterial is incubated in the differentiation medium, draining the differentiation medium from the elongate body, and replenishing the differentiation medium to re-submerge the ring of biomaterial. More optionally, the same apparatus may be re-used after removing the myofibres and cleaning the apparatus.

Optionally, the process comprises collecting at least one elongate body by removal of the elongate body from its respective at least one trough, said elongate body having a ring of biomaterial in the at least one circumferential groove. The elongate body having a ring of biomaterial in at least one circumferential groove may be collected by removal from the container and incubated elsewhere, preferable to a larger container. It may be noted that transferring the elongate body having a ring of biomaterial in at least one circumferential groove to a larger container allows freeing up of space, as the said elongate body may be placed positioned close to each other in the larger container for incubation.

Meanwhile, the first container (freed container, with troughs) may be drained of the medium and used mixture of the cells and the liquid hydrogel, cleaned, re-positioned and re-used for a next cycle of production of tissues from cells. More optionally, the process may require that a first part of the incubating is carried out for 1 to 4 days before collecting at least one elongate body by removal of the elongate body from its respective at least one trough, and a further part of the incubating is carried out after aforementioned collection. Notably, such incubation enables the formation of rings of tissues from the compaction of cells in the ring of biomaterial in the presence of differentiation medium.

In another embodiment, the at least one elongate body having a ring of tissue in the at least one circumferential groove may be collected by removing it from its respective at least one trough, after complete incubation as above. It will be appreciated that the ring of tissue is formed due to compaction of cells in the tissue. The compaction of tissues is achieved by the cell-induced pull-in of the extracellular matrix (ECM) and the consequent pushing-out of water molecules.

Optionally, the process further comprises positioning the elongate body to extend, by close-fitting relationship, centrally into one or more of the at least one trough, such that one of the troughs is aligned for filling adjacent an end of the elongate body. It may be noted that upon releasing the ring of tissue from the circumferential groove of the elongate body, the elongate body may be cleaned and re-used for the next cycle of tissue production from the refreshed mixture of cells and liquid hydrogel. In this regard, as mentioned previously, the cleaned elongate body is positioned by extending it centrally through one or more of the at least one trough, such that one of the troughs is aligned for filling adjacent an end of the elongate body.

Optionally, the process further comprises adding cells and liquid hydrogel into the aligned trough adjacent the end of the elongate body by means of a pipe. As mentioned previously, the mixture of cells and a liquid hydrogel may be added or re-filled into at least one trough of the apparatus by aligning trough adjacent the end of the elongate body by means of a pipe.

Optionally, the process further comprises moving the pipe and the elongate body to align with another of the at least one trough for filling. As mentioned previously, the concentric pipe and the elongate body may be aligned to fill another vertically adjacent (below or above) at least one trough for filling with the mixture of cells and the liquid hydrogel.

Optionally, the process further comprises adding cells and liquid hydrogel into the aligned trough adjacent the end of the elongate body by means of a pipe and moving the pipe and the elongate body to align with another of the at least one trough for filling, until each of the at least one trough is filled. In other words, re-filling each of the at least one or more troughs by moving the concentric arrangement of pipe and the elongate body by aligning it with another of the at least one trough for filling.

The process further comprises cutting the ring of tissue to release it from the elongate body. Upon the end of aforementioned incubation, the ring of tissue in at least one circumferential groove is transferred to a cutter for cutting the ring of tissue to release it from the elongate body. Optionally, the process requires cutting the ring of tissue to release it from the at least one circumferential groove of the elongate body. Optionally, the cutting is performed along the longitudinal groove of the elongate body. Specifically, a cutter is used to cut the ring of tissue from the circumferential grooves of the elongate body. More specifically, a longitudinal single cut may be made by running the cutter along the longitudinal groove carved out in one side of the elongate body. Such a single cut cleanly removes multiple rings of tissue from the elongate body. Furthermore, such clean removal of multiple rings of tissue is attributed to the depth of the longitudinal groove being comparable to the depth of the circumferential groove of the elongate body. Beneficially, cutting performed along the longitudinal groove of the elongate body ensures preserving the quality and structure of the muscle tissue so produced. Subsequently, the ring of tissue may be harvested and layered for production of the desired product, the bio artificial muscles.

Simultaneously, after removing the elongate body, having a ring of biomaterial in the at least one circumferential groove, from its respective at least one trough, the container may be cleaned, re-positioned and re-used by advancing at least one elongate body until a different one of the at least one of the circumferential grooves opens into the inner edge of the trough. The elongate body is carefully placed into the apparatus in a way that each lower circumferential groove visits the vertically adjacent above inner edge of the trough, while opening into the inner edge of the trough for a short duration of time. Optionally, the process may require that a first part of the incubating is carried out for 1 to 4 days before aforementioned advancing, and a further part of the incubating is carried out after such advancing. Furthermore, removal of the elongate body from the apparatus frees up the troughs for next cycle of cell growth, differentiation and ring formation.

Subsequently, optionally, the process comprises refilling the trough by transferring the cells in a mixture with a liquid hydrogel comprising a scaffolding biomaterial into the trough. As mentioned previously, troughs may be filled with a mixture of cells and liquid hydrogel, at an optimum temperature and for a predefined period of time, at a depth level to the inner edge of the troughs. This may be achieved using pipes that may be operable to extend in the separate of the laterally joined troughs, or extend centrally through the troughs while opening at a level of the opening of the outer wall of the trough to fill the same with the mixture.

Subsequently, the process comprises cutting the ring of tissue to release it from the at least one circumferential groove of the elongate body. The elongate body is again removed for harvesting the ring of tissue therefrom.

In an embodiment, the apparatus provided may have an elongate body in the form of a continuous loop. Optionally, the above process may be automated, using elongate body in the form of a continuous loop. More optionally, the continuous loop of elongate body comprising a plurality of circumferential grooves and a longitudinal groove, with depth comparable to the circumferential groove, may be operable to pass through the at least one trough in a continuous loop for a predefined period of time. The predefined period of time relates to the respective durations of time required for the different stages of tissue production from the cells in an optimum environment. Beneficially, the automation of the above process may reduce the repetitive labour required for filling troughs with biomaterial, harvesting and cutting the ring of tissue from the elongate body.

In an embodiment, the elongate body may be designed to include a longitudinal channel comprising side port opening into an end of the circumferential grooves to provide nutrients to and shuttling out the waste metabolites from the inner cells of the ring of tissue around each of the one or more circumferential grooves, reflective of the branched vascular network of the muscle tissue. Such optimization of the elongate body may be beneficial in preventing a necrotic core of the inner cells of the ring of tissue, while maintaining an optimal thickness of the tissue formed.

DETAILED DESCRIPTION OF DRAWINGS

Referring to FIG. 1, illustrated is a perspective view of an apparatus 100 for the production of tissue from cells, in accordance with an embodiment of the present disclosure. As shown, the apparatus 100 comprises an elongate body 102 having at least one circumferential groove, such as grooves 104. The apparatus 100 also comprise at least one trough, such as troughs 106 (better shown in FIG. 2). The elongate body 102 is operable to extend, by close-fitting relationship, centrally through at least one trough, i.e. the troughs 106. Further, as shown, the troughs 106 extend in a closed path. For example, as shown, the closed path is a circle, thereby providing at least one circular trough (such as the troughs 106) surrounding the elongate body 102.

Figure 2:
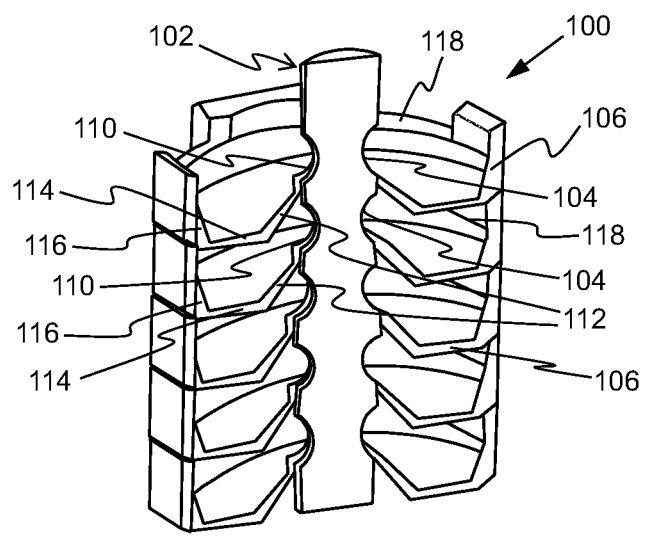
FIG. 2 is a cross-sectional view of the apparatus of FIG. 1, in accordance with an embodiment of the present disclosure.

Referring now to FIG. 2, illustrated is a cross sectional view of the apparatus 100 of FIG. 1, in accordance with an embodiment of the present disclosure. It will be appreciated that in FIG. 2, the elongate body 102 of FIG. 1 is shown to extend centrally through the troughs 106.

Further, the at least one of the circumferential grooves, such as the grooves 104, opens into an inner edge of a trough. For example, as shown, each of the grooves 104 of the elongate body 102 opens into an inner edge, such inner edges 110, of corresponding (or adjacent) troughs 106. Moreover, at least one trough has a sloping wall extending from a low region of the trough to the inner edge, and an outer wall extending from the low region to an outer edge of the trough. For example, as shown, each of the troughs 106 has a sloping wall 112 extending from a low region 114 to the inner edge 110. Further, each of the troughs 106 has an outer wall 116 extending from the low region 114 to an outer edge 118 of the troughs 106.

Figure 3:
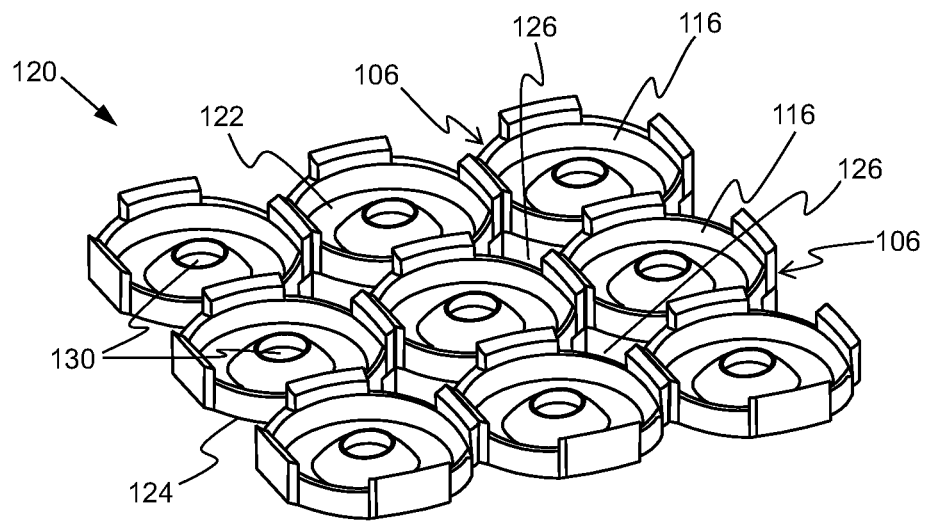
FIG. 3 is a perspective view of troughs for an apparatus, in accordance with an embodiment of the present disclosure.

FIG. 3 is a perspective view of troughs for an apparatus, such as the apparatus 100 of FIG. 1, in accordance with an embodiment of the present disclosure. As explained herein above with FIG. 1 that the apparatus 100 comprises at least one trough, specifically, the apparatus 100 includes a plurality of troughs, such as troughs 106. In present embodiment, the troughs 106 are joined edgewise outside their outer walls, such as the outer walls 116, to laterally-adjacent troughs. The troughs 106 are joined edgewise to form as a unitary component 120. The unitary component 120 includes a top surface 122 and a bottom surface 124. Further, the unitary component 120 has at least one through-hole, such as through-holes 126, communicating between the top surface 122 and the bottom surface 124. The through-holes 126 are located outside the outer walls 116 of the troughs 106. It will be appreciated that unitary component 120 (i.e. the troughs 106) also includes central holes, such as through-openings 130, operable to receive elongate bodies, such the elongate body 102 of FIG. 1, therethrough.

Figure 4:
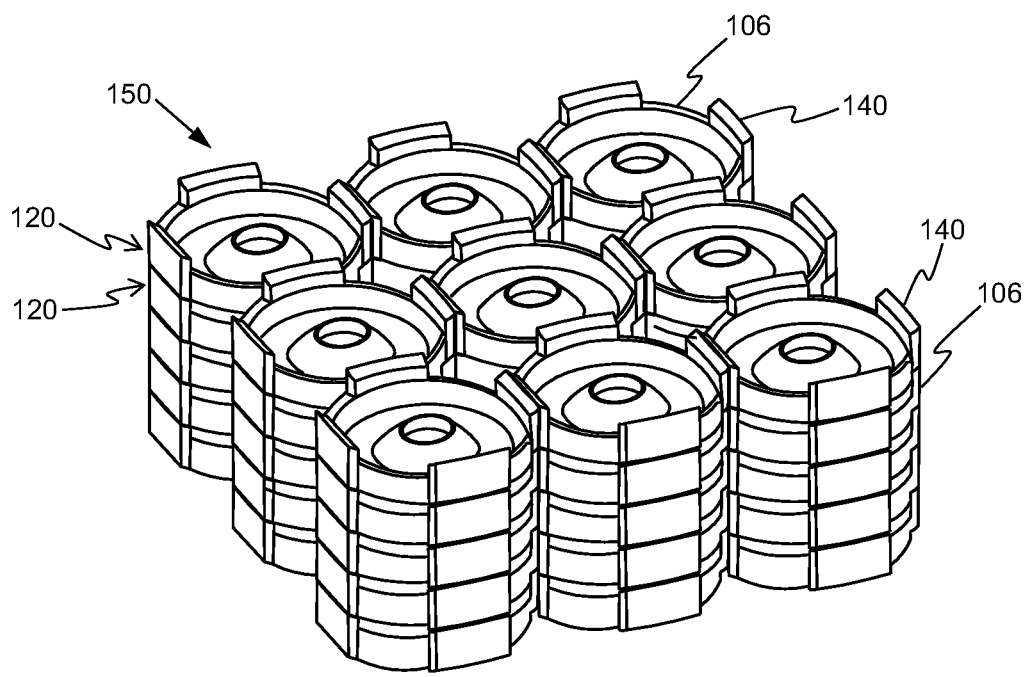
FIG. 4 is a perspective of the troughs of FIG. 3 in a stacked position, in accordance with an embodiment of the present disclosure.

Referring to FIG. 4, illustrated is a perspective of the troughs 106 of FIG. 3 in a stacked position, in accordance with an embodiment of the present disclosure. Specifically, a plurality of unitary components 120 of FIG. 3 is shown in the stacked position. Further, the at least one trough, such as the troughs 106, is provided with vertically extending spacers, such as spacers 140, to provide distance between adjacently stacked troughs 106. Moreover, at least one unitary component of troughs, such as the unitary components 120, is joined edgeways. The unitary components 120 are joined vertically to provide a grand unitary component 150, by joining the respective top surfaces, such as top surface 122 shown in FIG. 3, of the troughs 106 of the unitary components 120, with corresponding bottom surfaces, such as the bottom surface 124 shown in FIG. 3, of troughs 106 of an above-adjacent unitary component, such the unitary component 120.

Figure 5:
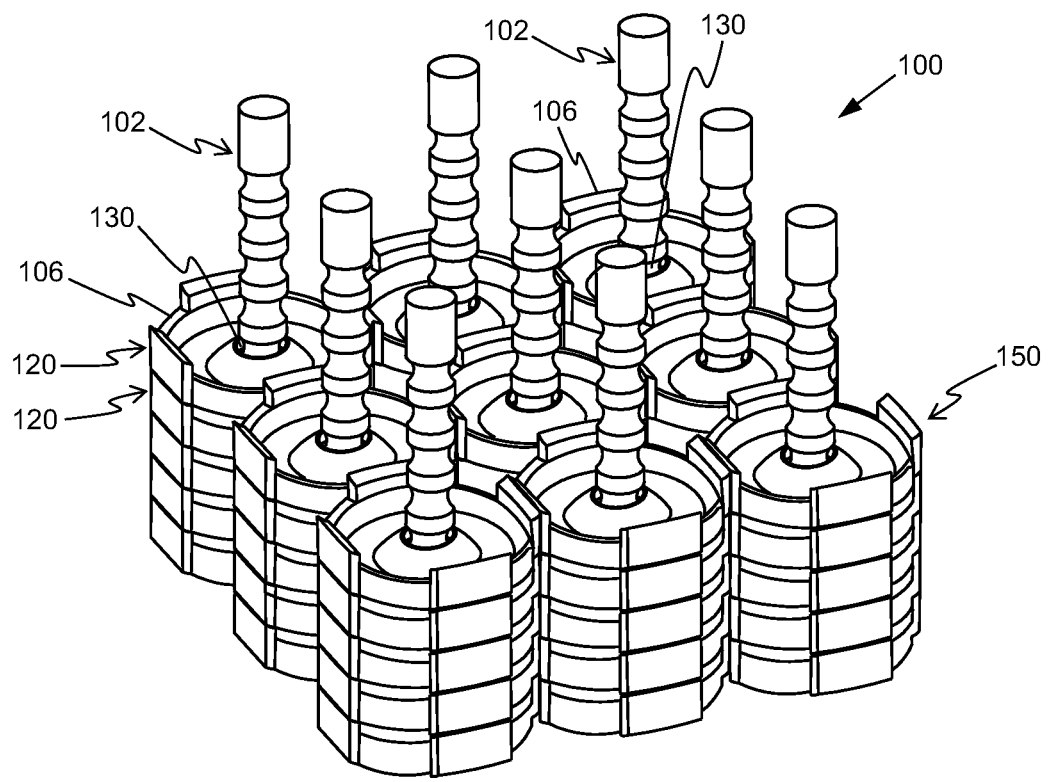
FIG. 5 is a perspective view an apparatus having a plurality of elongate bodies operable to extend centrally through a plurality of troughs, in accordance with another embodiment of the present disclosure.

Referring now to FIG. 5, illustrated is a perspective view an apparatus, such the apparatus 100, having a plurality of elongate bodies 102 operable to extend centrally through a plurality of troughs (such as the troughs 106 forming the unitary components 120), in accordance with another embodiment of the present disclosure. It will be appreciated that the apparatus 100 of FIG. 5 is formed by combining multiple units of apparatuses of FIG. 1. For example, the grand unitary component 150 (i.e. the stacked unitary components 120) is operable to receive the plurality of elongate bodies 102. Further, as mentioned herein above, the unitary components 120 also include central through-openings 130, operable to receive the elongate body 102 therethrough. This allows sliding engagement between the elongate body 102 and the troughs 106 for close-fitting relationship therebetween, as shown in FIG. 2.

Figure 6:
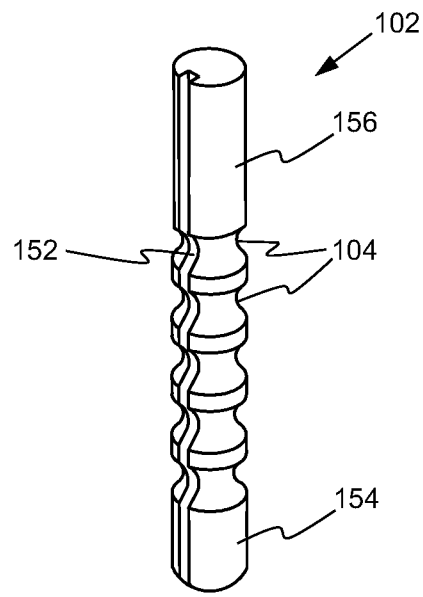
FIG. 6 is a perspective view of an elongate body of an apparatus, in accordance with an embodiment of the present disclosure.

FIG. 6 is a perspective view of an elongate body 102 of an apparatus (such as the apparatus 100 of FIG. 1), in accordance with an embodiment of the present disclosure. As shown, in an embodiment, the elongate body 102 is in the form of a pillar. For example, the elongate body 102 includes the at least one circumferential groove, such as circumferential grooves 104. As shown, the circumferential grooves 104 are spaced apart uniformly along a length of the elongate body 102, and each of the circumferential grooves 104 is designed to have a shape of a semi-circle. The elongate body 102 also includes a longitudinal groove 152 of at least the depth of the at least one circumferential groove 104. In an example, the longitudinal groove 152 is a rectangular-cut running along the length of the elongate body 102. The elongate body 102 also includes an insertion end 154 and a tail end 156 opposite to the insertion end 154.

Figure 7:
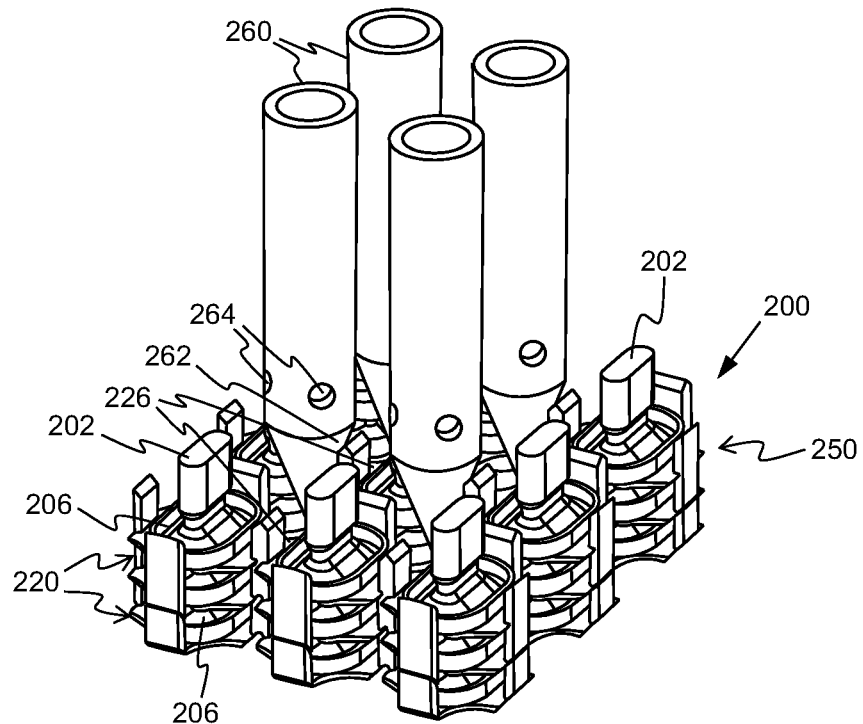
FIG. 7 is a perspective view of an apparatus for the production of tissue from cells, in accordance with yet another embodiment of the present disclosure.

FIG. 7 is a perspective view of an apparatus 200 for the production of tissue from cells, in accordance with yet another embodiment of the present disclosure. The apparatus 200 is substantially similar to the apparatus 100 of FIG. 5. For example, the apparatus 200 also includes at least one elongate body, such as elongate bodies 202, and at least one trough, such as troughs 206 (i.e. unitary components 220 stacked to form a grand unitary component 250). The elongate bodies 202 are shown centrally received by the unitary components 220. As shown, the troughs 206 extend in a closed path. In the present embodiment, the closed path is stadium-shaped, thereby providing at least one trough shaped like a track of a stadium surrounding the elongate bodies 202.

The apparatus 200 further comprises at least one pipe, such as pipes 260, having a closed end 262, and at least one side port, such as side ports 264, near the closed end 262. The pipes 260 are operable to extend through the at least one through hole, such as through holes 226, in the unitary components 220. The pipes 260 are used for adding a mixture of cells and a liquid hydrogel into the troughs 206 by the side ports 264. For example, the pipes 260 are operable to be received by the through holes 226 of the troughs 206, to align the side ports 264 with the troughs 206, and thereby adding the mixture of the cells and the liquid hydrogel into the troughs 206 through the side ports 264. The mixture of the cells and liquid hydrogel may be added to troughs of an apparatus using multiple other techniques, which will be explained herein later in conjunction with subsequent figures. It will be appreciated that the troughs 106 may be filled with the mixture of the cells and the liquid hydrogel to a depth level with inner edges (such as the inner edge 110, shown in FIG. 2) of the troughs 106.

Figure 8:
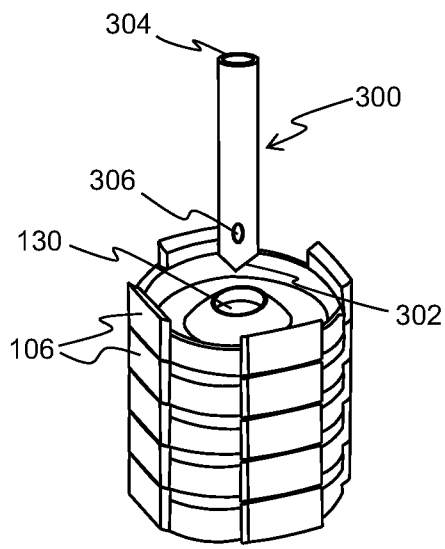
FIGS. 8-11 are schematic illustrations of various techniques for filling troughs of the apparatus, in accordance with various embodiments of the present disclosure.

FIGS. 8-11 are schematic illustrations of various techniques for filling troughs, such as troughs 106, of an apparatus, such as apparatus 100, in accordance with various embodiment of the present disclosure. As shown in FIG. 8, troughs, such as the troughs 106, are stacked, and the troughs 106 may be filled using a pipe 300. The pipe 300 includes a closed end 302, an open end 304 opposite to the closed end 302, and at least one side port, such as a side port 306, near the closed end 302. The pipe 300 is operable to be received by the through-openings, such as central through-openings 130, of the troughs 106 to align the side port 306 with the troughs 106, and thereby adding the cells and the liquid hydrogel into the troughs 106 through the side port 306. The pipe 300 may be received from a top or a bottom of the through-openings 130 for filling the troughs 106 with the mixture of the cells and the liquid hydrogen. It may be appreciated that the troughs 106 may be filled sequentially, along a vertically upward or downward direction.

Figure 9:
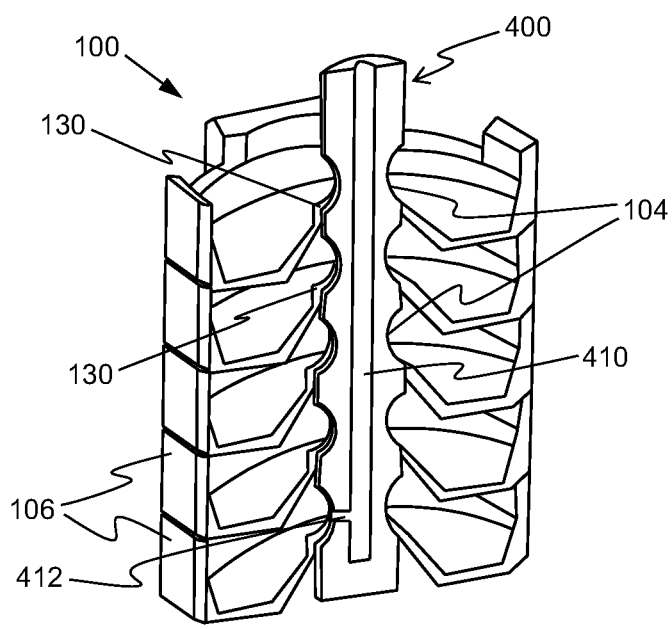

FIG. 9 illustrates a cross-sectional view of an elongate body 400 for an apparatus, such as the apparatus 100, in accordance with an embodiment of the present disclosure. The elongate body 400 is shown to be received inside centrally by the troughs 106 of the apparatus 100. The elongate body 400 includes the at least one circumferential groove, such as circumferential grooves 402. The elongate body 400 includes a longitudinal hole 410 and at least one side port 412 connected to the longitudinal hole 410. The elongate body 400 is operable to be received by the through-openings, such as central through-openings 130, to align the side port 412 with the troughs 106, and thereby adding the mixture of the cells and the liquid hydrogel into the troughs 106 through the side port 412 of the elongate body 400. Further, the troughs 106 may be initially stacked and thereafter may be filled sequentially.

Figure 10:
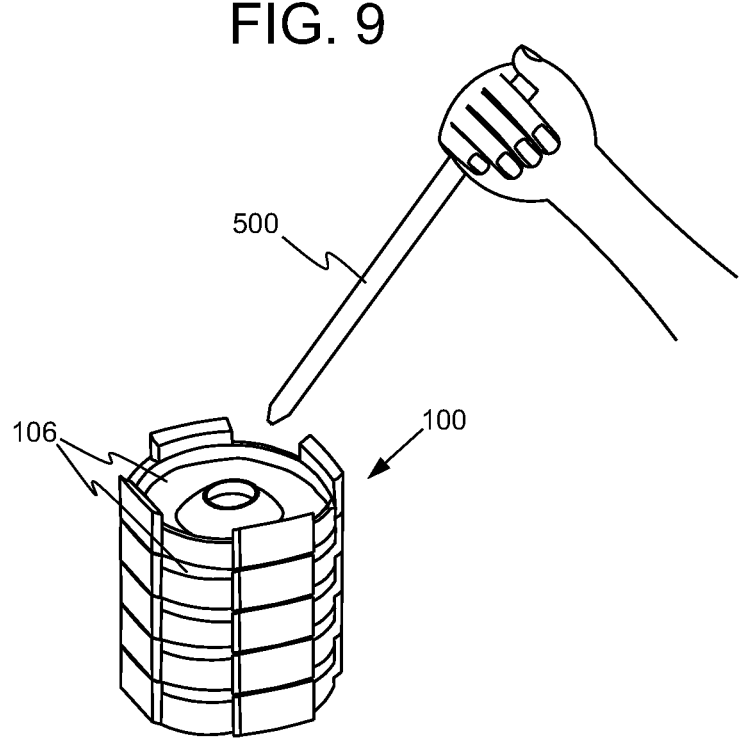

Referring now to FIG. 10, illustrated is a schematic drawing of a pipette 500 to be used for filling troughs, such as troughs 106, as the apparatus 100, in accordance with an embodiment of the present disclosure. It will be appreciated that the troughs 106 may be filled with the mixture of the cells and the liquid hydrogel using the pipette 500. Further, the troughs 106 may be filled sequentially and stacked thereafter.

Figure 11:
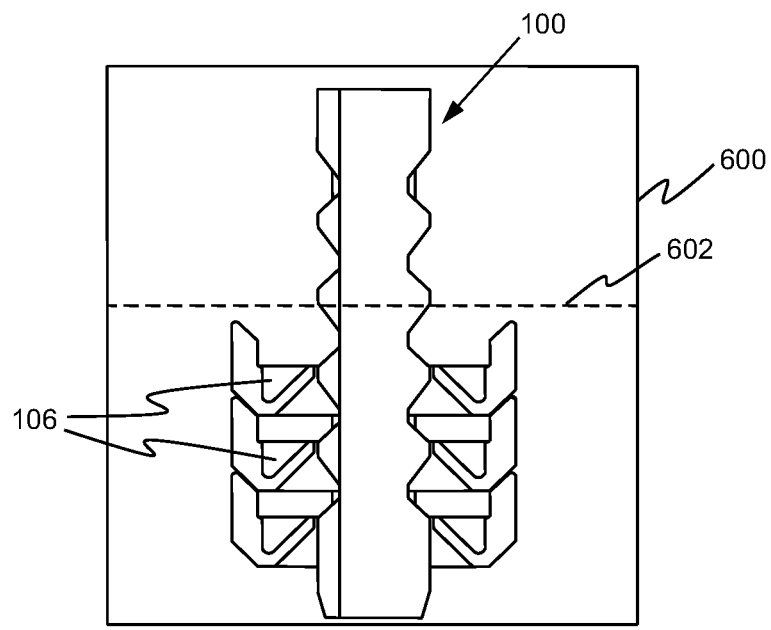

Referring now to FIG. 11, illustrated is a schematic drawing of a container 600 to be used for filling troughs, such as the troughs 106, of an apparatus, such as the apparatus 100, in accordance with an embodiment of the present disclosure. It will be appreciated that the troughs 106 may be filled with a mixture 602 of cells and liquid hydrogel by submerging the troughs 106 into the container 600 filled with the mixture 602.

FIGS. 12-17 are schematic illustrations of steps of a process for the production of tissue from cells, in accordance with an embodiment of the present disclosure. The process uses an apparatus, such as the apparatus 100 or 200, for the production of tissue from the cells.

Figure 12:
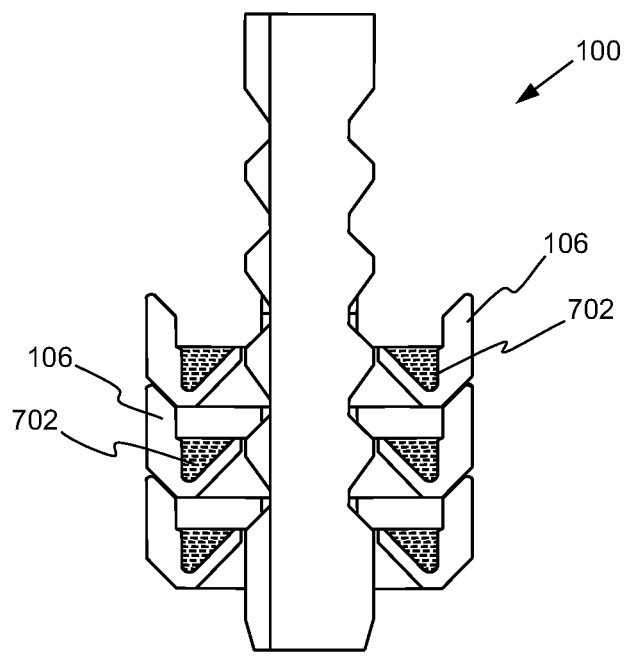
FIGS. 12-17 are schematic illustrations of steps of a process for the production of tissue from cells, in accordance with an embodiment of the present disclosure.
Figure 13:
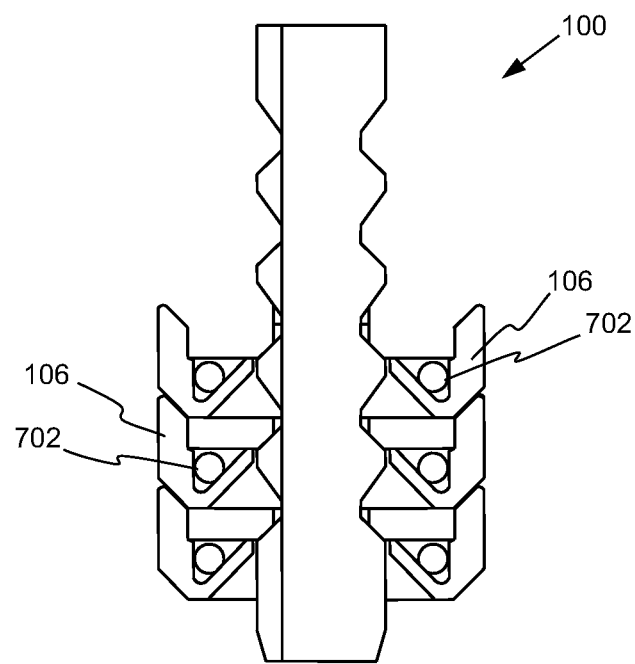
Figure 14:
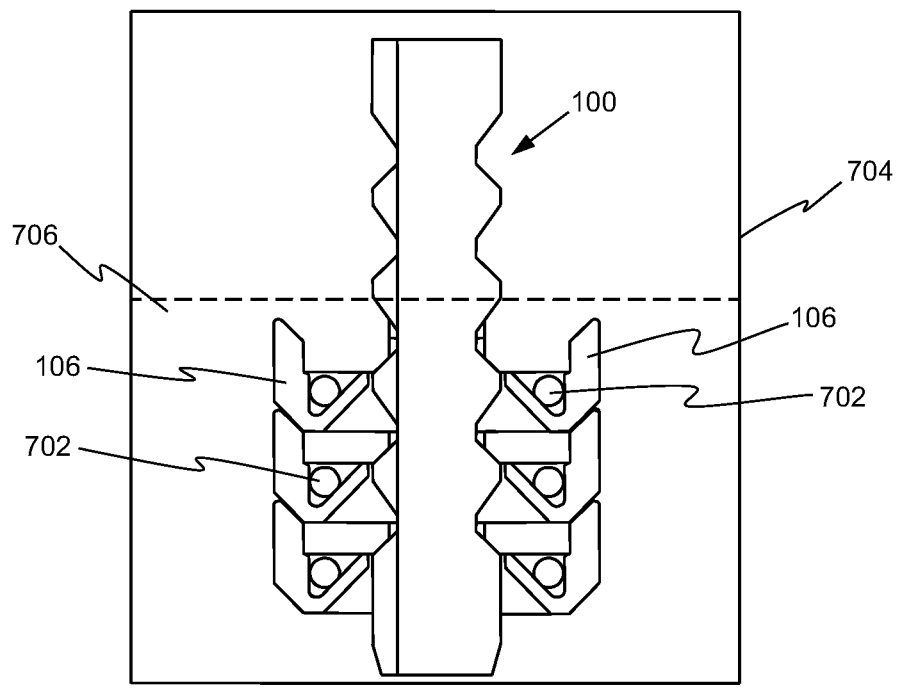
Figure 15:
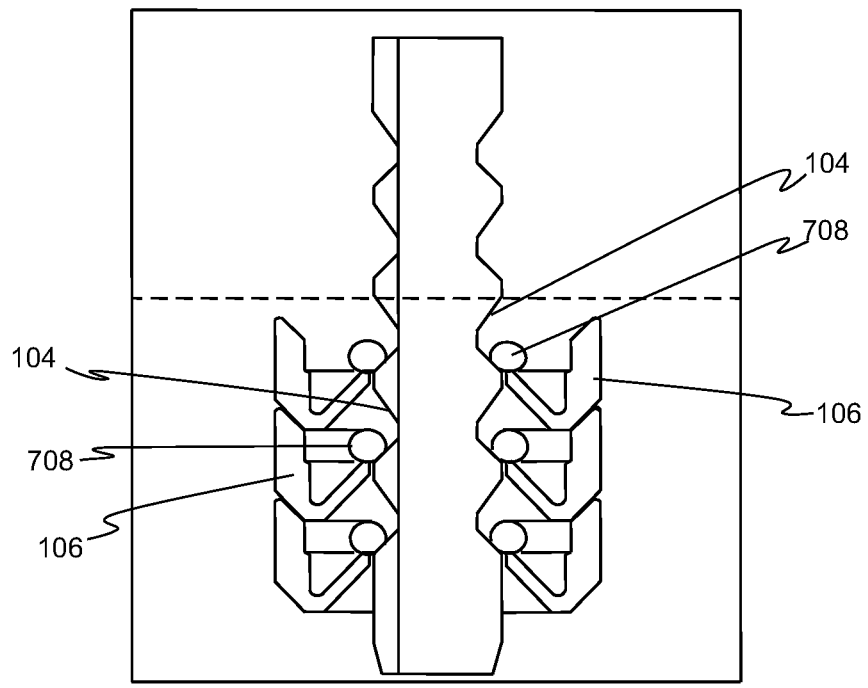
Figure 16:
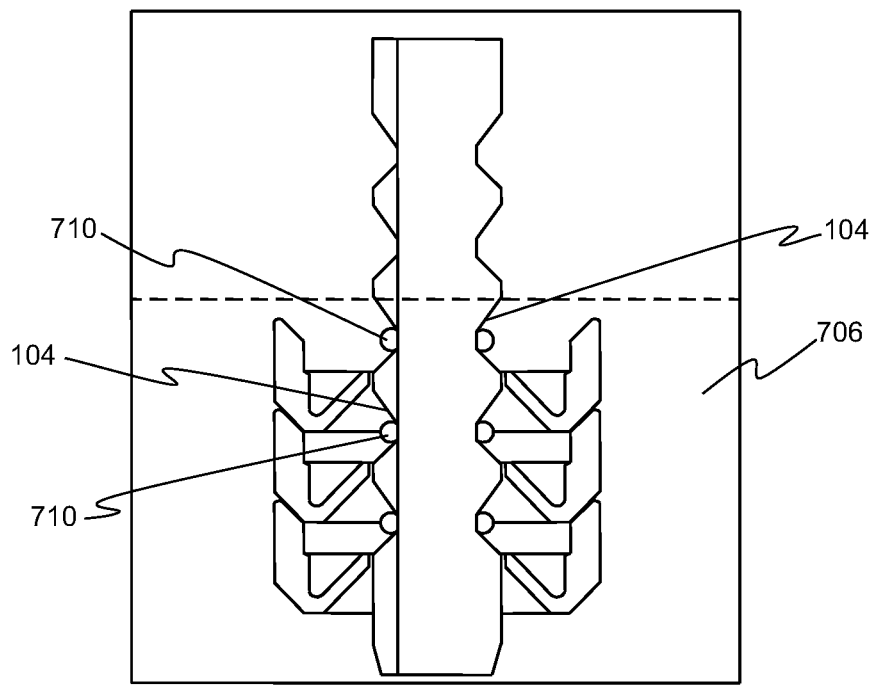
Figure 17:
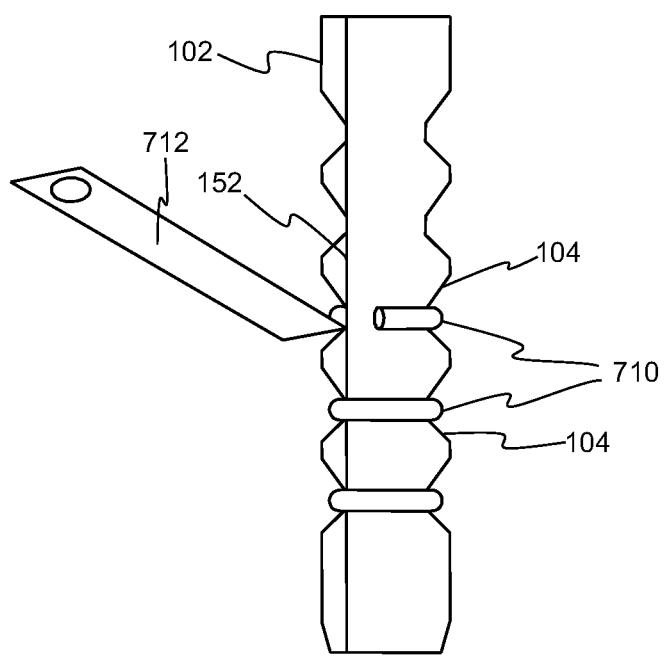

Therefore, for the process initially an apparatus, such as the apparatus 100, is provided, as shown in FIG. 12. Further, as shown in FIG. 12, a mixture 702 of the cells and the liquid hydrogel is added to at least one trough, such as the troughs 106, of the apparatus 100. Referring now to FIG. 13, illustrated is the apparatus 100 with the troughs 106 filled with the mixture 702 of the cells and the liquid hydrogel. However, as shown in FIG. 13, the mixture 702 of the cells and the liquid hydrogel solidifies with the cross-linking of scaffolding biomaterial present in the liquid hydrogel. In an example, the solidification of the mixture 702 of the cells and the liquid hydrogel takes place in an hour. Further, as shown in FIG. 14, illustrated is the apparatus 100 with the troughs 106, filled with the solidified mixture 702 of the cells and the liquid hydrogel, submerged into a container 704 filled with a differentiation medium 706. In the process, the apparatus may be lowered into the container before filling the container with a differentiation medium. The solidified mixture 702 of the cells and the liquid hydrogel is one of the stages of a transitioning intermediate. Referring now to FIG. 15, depicted is the migration of transitioning intermediate 708 from the solidified mixture 702 (shown in FIG. 14) of the cells and the liquid hydrogel. The migration of the transitioning intermediate 708 from the trough 106 and into the circumferential groove in the pillar takes place in 2 or 3 days. Further, the transitioning intermediate 708 is shown to migrate from the troughs 106 to the circumferential grooves 104 due to cell-induced compaction, i.e. after cross-linking of the scaffolding biomaterial. Referring now to FIG. 16, depicted is the incubation of the transitioning intermediate 708 (shown in FIG. 15) to form tissue. As shown in FIG. 16, the transitioning intermediate 708 of FIG. 15 is shown to incubate in the differentiation medium 706 to form tissue 710 comprised in a ring in the circumferential grooves 104. In an example, the incubation of said tissue 710 (into ring form) may take place in 2-4 weeks. Referring now to FIG. 17, illustrated is cutting of rings of tissue 710 to release it from the circumferential grooves 104 of the elongate body 102. As shown, the cutting may be performed using a cutter 712, such as a blade or water cutter. Further, the cutting is performed along the longitudinal groove 152 of the elongate body 102.

Figure 18:
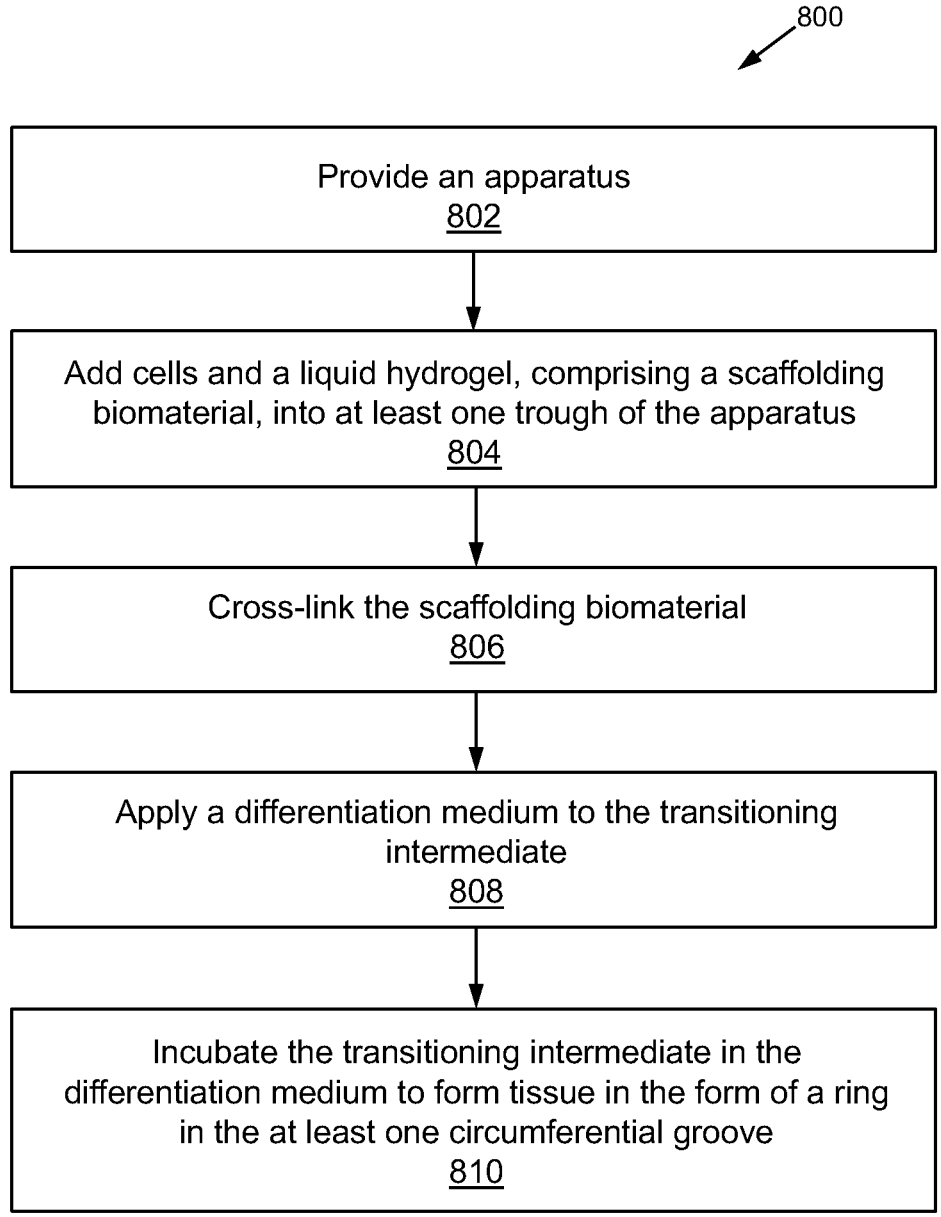
FIG. 18 is a block diagram depicting steps of a process for production of tissue from cells, via a transitioning intermediate which transitions from the cells into the tissue, in accordance with an embodiment of the present disclosure.

FIG. 18 is a block diagram depicting steps of a process 800 for production of tissue from cells, via a transitioning intermediate which transitions from the cells into the tissue, in accordance with an embodiment of the present disclosure.

It will be appreciated that the process 800 is implemented with a use of an apparatus, such as one of the apparatuses 100, 200, shown and explained in conjunction with FIGS. 1-17.

At step 802, an apparatus, according to aforementioned text i.e. shown and explained in conjunction with FIGS. 1-17, is provide. At step 804, cells and liquid hydrogel, comprising a scaffolding biomaterial, is added into at least one trough of the apparatus. At step 806, the scaffolding biomaterial is allowed to cross-link. At step 808, a differentiation medium is applied to the transitioning intermediate. At step 810, the transitioning intermediate is incubated in the differentiation medium to form tissue comprised in a ring in the at least one circumferential groove.

The steps 802 to 810 are only illustrative and other alternatives can also be provided where one or more steps are added, one or more steps are removed, or one or more steps are provided in a different sequence without departing from the scope of the claims herein. For example, in the process 800 the cells are added to the hydrogel before adding into the at least one trough. Optionally, in the process 800 the differentiation medium is rejuvenated after at least one part of the period of incubation. The process 800 may comprise collecting at least one elongate body by removal of the elongate body from its respective at least one trough, said elongate body having the ring of biomaterial in the at least one circumferential groove. Moreover, the process 800 further comprises cutting the ring of tissue to release it from the elongate body. Optionally, the process 800 further comprises positioning the elongate body to extend, by close-fitting relationship, centrally into one or more of the at least one trough, such that one of the troughs is aligned for filling adjacent an end of the elongate body; adding the cells and the liquid hydrogel into the aligned trough adjacent the end of the elongate body by means of a pipe; moving the pipe and the elongate body to align with another of the at least one trough for filling; and repeating, the addition of cells and liquid hydrogel into troughs and moving the pipe and the elongate body, until each of the at least one trough is filled.

Modifications to embodiments of the present disclosure described in the foregoing are possible without departing from the scope of the present disclosure as defined by the accompanying claims. Expressions such as "including", "comprising", "incorporating", "have", "is" used to describe and claim the present disclosure are intended to be construed in a non-exclusive manner, namely allowing for items, components or elements not explicitly described also to be present. Reference to the singular is also to be construed to relate to the plural.

The invention claimed is:

1. An apparatus for production of tissue from cells, the apparatus comprising at least one elongate body having at least one circumferential groove and extending, by close-fitting relationship, centrally through at least one trough, the at least one trough extending in a closed path, the at least one circumferential groove opening into an inner edge of the at least one trough.

2. The apparatus according to claim 1, wherein the closed path is a circle, thereby providing at least one circular trough surrounding the elongate body.

3. The apparatus according to claim 1, wherein the at least one trough has a sloping wall extending from a low region of the at least one trough to the inner edge, and an outer wall extending from the low region to an outer edge of the at least one trough.

4. The apparatus according to claim 1, wherein the at least one trough further comprises a plurality of troughs, the at least one elongate body further comprises a plurality of elongate bodies and separate elongate bodies extend, respectively, through separate troughs.

5. The apparatus according to claim 4, wherein two or more troughs of the plurality are joined edgewise outside their outer walls.

6. The apparatus according to claim 5, wherein joined troughs are formed as a unitary component having a top surface and a bottom surface.

7. The apparatus according to claim 4, wherein two or more troughs of the plurality are joined edgewise outside their outer walls into a first unitary component and two or more troughs of the plurality are joined edgewise outside their outer walls into a second unitary component and respective top surfaces of troughs of the first unitary component are joined with corresponding bottom surfaces of troughs of the second unitary component to provide a grand unitary component.

8. The apparatus according to claim 1, wherein the at least one elongate body further comprises a longitudinal groove having a depth equal to a depth of the at least one circumferential groove.

9. The apparatus according to claim 1, wherein each of the circumferential grooves opens into the inner edge of the at least one trough.

10. The apparatus according to claim 1, wherein the close-fitting relationship between the elongate body and the at least one trough comprises a sliding engagement.

11. A process for the production of tissue from cells, via a transitioning intermediate which transitions from the cells into the tissue, the process comprising: providing an elongate body having one or more circumferential grooves and being operable to extend, by close-fitting relationship, centrally through one or more troughs, the one or more troughs extending in a closed path, at least one of the one or more circumferential grooves opening into an inner edge of one of the one or more troughs; adding the cells and a liquid hydrogel, comprising a scaffolding biomaterial, into at least one of the one or more troughs; cross-linking the scaffolding biomaterial; applying a differentiation medium to the transitioning intermediate; and incubating the transitioning intermediate in the differentiation medium to form tissue comprised in a ring in the at least one circumferential groove.

12. The process according to claim 11, wherein the formed tissue comprises myofibres.

13. The process according to claim 11, wherein the cells are selected from at least one of the group consisting of mesenchymal cells, myoblasts and myocytes.

14. The process according to claim 11, wherein the transitioning intermediate migrates from the at least one trough to the at least one circumferential groove after the cross-linking.

15. The process according to claim 11, wherein the cells are added to the hydrogel before adding into the at least one trough.

16. The process according to claim 11, further comprising, after at least part of the incubating, rejuvenating the differentiation medium by at least one of i) oxygenating, ii) adding at least one nutrient, iii) removing particulate matter, and iv) exchanging the differentiation medium with a fresh differentiation medium.

17. The process according to claim 11, further comprising collecting the formed tissue by removing the elongate body from its respective at least one trough.

18. The process according to claim 17, further comprising cutting the ring of tissue to release it from the elongate body.

19. The process according to claim 18, wherein the cutting is performed along a longitudinal groove of the elongate body.

20. The process according to claim 11, further comprising adding the cells and liquid hydrogel into the at least one trough with at least one pipe having a closed end, a side port near the closed end, and operable to extend movably outside the outer walls of the at least one trough and/or centrally through the at least one trough such that the side port is aligned in fluid communication with at least one of the one or more troughs.

* * * * *